US010286006B2

(12) United States Patent
Laurie et al.

(10) Patent No.: US 10,286,006 B2
(45) Date of Patent: May 14, 2019

(54) TRACE ELEMENTS

(71) Applicant: WARBURTON TECHNOLOGY LIMITED, Dublin (IE)

(72) Inventors: Robert N. Laurie, Somerset West (ZA); William A. Smith, Dublin (IE)

(73) Assignee: WARBURTON TECHNOLOGY LIMITED, Dublin (IE)

( * ) Notice: Subject to any disclaimer, the term of this patent is extended or adjusted under 35 U.S.C. 154(b) by 0 days.

(21) Appl. No.: 15/165,773

(22) Filed: May 26, 2016

(65) Prior Publication Data

US 2016/0271176 A1 Sep. 22, 2016

Related U.S. Application Data

(60) Continuation of application No. 13/759,454, filed on Feb. 5, 2013, now abandoned, which is a division of application No. 11/574,692, filed as application No. PCT/IB2005/052917 on Sep. 7, 2005, now Pat. No. 8,377,482.

(30) Foreign Application Priority Data

Sep. 9, 2004 (ZA) .................................. 2004/7201

(51) Int. Cl.
| | | |
|---|---|---|
| A61K 31/57 | (2006.01) | |
| A61K 33/04 | (2006.01) | |
| A61K 33/24 | (2019.01) | |
| A61K 33/26 | (2006.01) | |
| A61K 33/30 | (2006.01) | |
| A61K 33/32 | (2006.01) | |
| A61K 33/34 | (2006.01) | |
| A61K 31/095 | (2006.01) | |
| A61K 31/167 | (2006.01) | |
| A61K 31/365 | (2006.01) | |
| A61K 31/429 | (2006.01) | |
| A61K 31/565 | (2006.01) | |
| A61K 31/568 | (2006.01) | |
| A61K 31/4184 | (2006.01) | |
| A61K 31/7048 | (2006.01) | |
| A61K 39/00 | (2006.01) | |
| A61K 31/00 | (2006.01) | |
| A61K 45/06 | (2006.01) | |
| A61K 33/00 | (2006.01) | |
| A61K 9/00 | (2006.01) | |
| A61K 9/08 | (2006.01) | |
| A61K 33/18 | (2006.01) | |
| A61K 47/10 | (2017.01) | |
| A61K 47/18 | (2017.01) | |

(52) U.S. Cl.
CPC ............ *A61K 33/34* (2013.01); *A61K 9/0019* (2013.01); *A61K 9/08* (2013.01); *A61K 31/00* (2013.01); *A61K 31/095* (2013.01); *A61K 31/167* (2013.01); *A61K 31/365* (2013.01); *A61K 31/4184* (2013.01); *A61K 31/429* (2013.01); *A61K 31/565* (2013.01); *A61K 31/568* (2013.01); *A61K 31/57* (2013.01); *A61K 31/7048* (2013.01); *A61K 33/00* (2013.01); *A61K 33/04* (2013.01); *A61K 33/18* (2013.01); *A61K 33/24* (2013.01); *A61K 33/26* (2013.01); *A61K 33/30* (2013.01); *A61K 33/32* (2013.01); *A61K 39/00* (2013.01); *A61K 45/06* (2013.01); *A61K 47/10* (2013.01); *A61K 47/183* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,740,373 | A * | 4/1988 | Kesselman | .......... A61K 9/0019 424/638 |
| 6,165,987 | A * | 12/2000 | Harvey | ................ A61K 9/0019 514/248 |
| 2002/0068079 | A1* | 6/2002 | Laurie | .................. A61K 9/0019 424/422 |
| 2004/0047894 | A1* | 3/2004 | Kramer | ................. A61K 31/20 424/439 |

(Continued)

OTHER PUBLICATIONS

Webster's New World Dictionary, 2nd college ed., The World Publishing Co., New York, p. 1127 (1972).*

(Continued)

*Primary Examiner* — John Pak
(74) *Attorney, Agent, or Firm* — Stephen J. Weyer, Esq.; Stites & Harbison, PLLC

(57) ABSTRACT

A trace element solution comprises at least one metal selected from the group comprising selenium, copper, zinc, manganese and chromium; and at least one component selected from the group comprising a vitamin, a vaccine, a growth stimulant, a dewormer, iron dextran, an antibiotic and a synchronization preparation. The synchronization preparation is a combination of injectable hormonal preparations, inplantable hormonal preparations, intravaginal hormonal preparation and other slow release hormonal preparation. The antibiotics include oral, injectable and implantable therapeutic remedies. The vaccine includes antigens and a combination of antigens and adjuvants. The growth stimulants include zeranol, estradiol, testosterone, progesterone and trenbolone acetate. The dewormer includes macrocyclic lactones, leramizoles, benzimidazoles and salicylanilides. The macrocyclic lactones include doramectin, ivermectin, abamectin and moxidectin.

8 Claims, No Drawings

(56) References Cited

U.S. PATENT DOCUMENTS

| | | | |
|---|---|---|---|
| 2006/0128641 A1* | 6/2006 | Holmes | A61K 9/0014 |
| | | | 514/28 |
| 2008/0102074 A1* | 5/2008 | Laurie | A61K 31/00 |
| | | | 424/184.1 |

OTHER PUBLICATIONS

Chlorocresol Summary Report. The European Agency for the Evaluation of Medicinal Products, Committee for Veterinary Medicinal Products, summary report. Chlorocresol [online], pp. 1-3, Mar. 1996 [retrieved on Jan. 18, 2007]. Retrieved from the Internet: <http://www.emea.eu.int.pdfs/vet/mrls/007496en.pdf>.*

* cited by examiner

TRACE ELEMENTS

CROSS REFERENCE TO RELATED APPLICATION

This application is a continuation of U.S. application Ser. No. 13/759,454, filed Feb. 5, 2013, which is a divisional of U.S. application Ser. No. 11/574,692, filed Aug. 2, 2007, which is a 371 Application of PCT/IB2005/052917, filed Sep. 7, 2007, and issued as U.S. Pat. No. 8,377,482 on Feb. 19, 2013 all herein incorporated by reference.

FIELD OF INVENTION

The present invention relates to trace elements.

BACKGROUND TO INVENTION

It has been found that there is a deficiency/sub-optimal level of certain trace elements in feed raw material used for livestock production in particular areas around the world. Various suggestions have been made to provide the required trace elements to such animals. Different chemical compounds and complexes have been investigated for applying the trace elements by way of feed supplements, licks, drenches or injections.

In general the problem with injectable solutions is that the concentration of the minerals in the solutions is too low. This means that relatively large quantities have to be injected, which in turn causes tissue damage and can cause abscesses at the injection site. Furthermore, it is generally the case that different trace elements are often simultaneously deficient. Most injectable trace element solutions provide a supplement of individual trace elements. This means that two or more trace element solutions have to be provided by way of separate injections.

ZA 1982/6778 (Laurie) discloses a trace element solution and a method of providing the trace elements to livestock. This trace element solution includes ethylene diamino tetra acetic acid complexes of the required mineral in suitable quantities. However, the trace element solution includes no selenium or selenite compound.

In the specification and claims the expression EDTA refers to ethylene diaminotetraacetic acid ($C_{10}H_{16}O_8N_2$ or $(HO_2CH_2C)_2NCH_2CH_2N$—$(CH_2CO_2H)_2$).

U.S. Pat. No. 4,335,116 (Howard) discloses mineral-containing therapeutic compositions containing EDTA complexes of trace elements. Notably, U.S. Pat. No. 4,335,116 utilises tetra-sodium EDTA, a selenium glycine complex, and metal chlorides for the preparation of the EDTA complexes. Unfortunately, the chloride ions cause contamination and each complex solution is to be made individually. Furthermore, overnight time is required for complexing and heating up afterward to speed up the process, requires extra apparatus. If mixtures are required, the individual solutions are to be blended. If various concentrations as well as compositions are to be made, it can only be done in a cumbersome way, requiring extra apparatus. A further problem may arise when mixtures of high concentration are needed. In certain cases it would be impossible to deliver them, because mixing is always accompanied by dilution.

U.S. Pat. No. 6,638,539 (Laurie et al) discloses a method of preparing a trace element solution, which includes the steps of providing at least one EDTA-complex, of providing a sodium selenite solution, and of combining the EDTA-complexes and the sodium selenite solution. However, the method enables production of a trace element solution of only about 55 mg/ml.

It is an object of the invention to suggest methods and means for overcoming these problems.

SUMMARY OF INVENTION

According to the invention, a trace element solution comprises
(a) at least one metal selected from the group comprising selenium, copper, zinc, manganese and chromium; and
(b) at least one component selected from the group comprising a vitamin, a vaccine, a growth stimulant, a dewormer, iron dextran, an antibiotic and a synchronisation preparation.

The synchronisation preparation may be a combination of injectable hormonal preparations, inplantable hormonal preparations, intravaginal hormonal preparation and/or other slow release hormonal preparation.

The antibiotic(s) may include oral, injectable and/or implantable therapeutic remedies.

The antibiotic(s) may be used to treat and/or prevent infectious diseases.

The vaccine may include antigens and/or a combination of antigens and adjuvants.

The growth stimulants may include zeranol, estradiol, testosterone, progesterone and/or trenbolone acetate.

The dewormer may include macrocyclic lactones, leramizoles, benzimidazoles and/or salicylanilides.

The macrocyclic lactones may include doramectin, ivermectin, abamectin and/or moxidectin.

The solution may comprise a concentration of the metal(s) of at least 20 to 60 mg/ml.

The solution may comprise at least one compound selected from the group comprising iodine, potassium iodide, sodium iodide, iron, iron chloride, zinc oxide, manganese sulphate, sodium selenite, copper carbonate, sodium carbonate, $ZnNa_2EDTA$, $MnNa_2EDTA$, $CuNa_2EDTA$, $CrNa_2EDTA$, iron dextran, $FeNa_2EDTA$, anhydrous disodium EDTA and sodium hydroxide.

At least one of the metal(s) may be provided in the form of an EDTA complex.

The EDTA complex may be obtained by means of at least one compound selected from the group comprising sodium EDTA, sodium hydroxide EDTA acid and potassium EDTA.

The solution may comprise chloro-cresol as preservative.

The solution may be prepared in a continuous batch process.

The solution may be an injectable solution.

The solution may be a drenchable solution.

Also according to the invention, a method of preparing a trace element solution comprising at least one metal selected from the group comprising selenium, copper, zinc, manganese and chromium, said method including the steps of:
(a) preparing a $MnCO_3$ mixture in a container;
(b) adding an EDTA solution to the container and subsequently adding at least one metal compound;
(c) adding $Na_2SeO_3$ to the container to obtain the trace element solution; and
(d) adding at least one component selected from the group comprising a vitamin, a vaccine, a growth stimulant, a dewormer, iron dextran, an antibiotic and a synchronisation preparation.

The synchronisation preparation may be a combination of injectable hormonal preparations, inplantable hormonal preparations, intravaginal hormonal preparation and/or other slow release hormonal preparation.

The antibiotic(s) may include oral, injectable and/or implantable therapeutic remedies.

The antibiotic(s) may be used to treat and/or prevent infectious diseases.

The vaccine may include antigens and/or a combination of antigens and adjuvants.

The growth stimulants may include zeranol, estradiol, testosterone, progesterone and/or trenbolone acetate.

The dewormer may include macrocyclic lactones, leramizoles, benzimidazoles and/or salicylanilides.

The macrocyclic lactones may include doramectin, ivermectin, abamectin and/or moxidectin.

The solution may comprise a concentration of the metal(s) of at least 60 mg/ml.

The EDTA solution may be selected from the group comprising a potassium EDTA solution and a sodium EDTA solution.

The method may comprise the step of adding $CrCl_3.6H_2O$ to the trace element solution.

The method may comprise the step of adding a EDTA/NaOH mixture prior to addition of the $CrCl_3.6H_2O$ to the trace element solution.

The method may comprise the step of adjusting the pH of the trace element solution to 6.7 to 7.0.

The method may comprise the step of adjusting the pH of the trace element solution by adding at least one compound selected from the group comprising NaOH and EDTA.

The trace element solution may be diluted.

The temperature of the $MnCO_3$ mixture may be at least 60 degrees Celsius.

Water having a temperature of at least 70 degrees Celsius may be added to the $MnCO_3$ mixture.

The addition of the EDTA/NaOH mixture may occur gradually with small quantities.

The method may comprise the step of cooling the trace element solution prior to addition of the $Na_2SeO_3$.

The $MnCO_3$ mixture may be prepared by mixing $MnSO_4$ and $Na_2CO_3$.

The metal compound may be selected from the group comprising ZnO, $CuCO_3$, $Na_2CO3$, $MnSO_4$ and $FeCl_3$.

The metal compound may be selected from the group comprising metal oxides, metal hydroxides and metal carbonates.

Yet further according to the invention, there is provided a trace element solution when prepared by the above method.

Yet further according to the invention, there is provided a stock lick, which comprises a trace element solution when prepared by the above method.

Yet further according to the invention, a method of providing trace elements to animals, such as livestock, comprises the steps of preparing a trace element solution as described above and of providing the solution in a suitable quantity to an animal.

Yet further according to the invention, there is provided an injectable trace element solution, which comprises at least one compound selected from the group comprising iodine, potassium iodide and sodium iodide and which comprises a concentration of the compound(s) of at least 20 to 60 mg/ml and at least one component selected from the group comprising a vitamin, a vaccine, a growth stimulant, a dewormer, iron dextran, an antibiotic and a synchronisation preparation.

The synchronisation preparation may be a combination of injectable hormonal preparations, inplantable hormonal preparations, intravaginal hormonal preparation and/or other slow release hormonal preparation.

The antibiotic(s) may include oral, injectable and/or implantable therapeutic remedies.

The antibiotic(s) may be used to treat and/or prevent infectious diseases.

The vaccine may include antigens and/or a combination of antigens and adjuvants.

The growth stimulants may include zeranol, estradiol, testosterone, progesterone and/or trenbolone acetate.

The dewormer may include macrocyclic lactones, leramizoles, benzimidazoles and/or salicylanilides.

The macrocyclic lactones may include doramectin, ivermectin, abamectin and/or moxidectin.

Yet further according to the invention, there is provided a trace element solution, which comprises at least one compound selected from the group comprising chromium, chromium EDTA complex, chromium sodium EDTA complex, chromium calcium EDTA complex, chromium potassium EDTA complex and $CrCl_3.6H_2O$ and at least one component selected from the group comprising a vitamin, a vaccine, a growth stimulant, a dewormer, iron dextran, antibiotic and a synchronisation preparation.

The synchronisation preparation may be a combination of injectable hormonal preparations, inplantable hormonal preparations, intravaginal hormonal preparation and/or other slow release hormonal preparation.

The antibiotic(s) may include oral, injectable and/or implantable therapeutic remedies.

The antibiotic(s) may be used to treat and/or prevent infectious diseases.

The vaccine may include antigens and/or a combination of antigens and adjuvants.

The growth stimulants may include zeranol, estradiol, testosterone, progesterone and/or trenbolone acetate.

The dewormer may include macrocyclic lactones, leramizoles, benzimidazoles and/or salicylanilides.

The macrocyclic lactones may include doramectin, ivermectin, abamectin and/or moxidectin.

Yet further according to the invention, a trace element solution
(a) comprises at least one metal selected from the group comprising selenium, copper, zinc, manganese and chromium;
(b) comprises at least one of the metal(s) provided in the form of an EDTA complex;
(c) which is obtained by at least one compound selected from the group comprising iodine, potassium iodide, sodium iodide, iron, iron chloride, zinc oxide, manganese sulphate, sodium selenite, copper carbonate, sodium carbonate, $ZnNa_2EDTA$, $MnNa_2EDTA$, $CuNa_2EDTA$, $CrNa_2EDTA$, iron dextran, $FeNa_2EDTA$, anhydrous disodium EDTA and sodium hydroxide; and
(d) at least one component selected from the group comprising a vitamin, a vaccine, a growth stimulant, a dewormer, iron dextran, an antibiotic and a synchronisation preparation.

The synchronisation preparation may be a combination of injectable hormonal preparations, inplantable hormonal preparations, intravaginal hormonal preparation and/or other slow release hormonal preparation.

The antibiotic(s) may include oral, injectable and/or implantable therapeutic remedies.

The antibiotic(s) may be used to treat and/or prevent infectious diseases.

The vaccine may include antigens and/or a combination of antigens and adjuvants.

The growth stimulants may include zeranol, estradiol, testosterone, progesterone and/or trenbolone acetate.

The dewormer may include macrocyclic lactones, leramizoles, benzimidazoles and/or salicylanilides.

The macrocyclic lactones may include doramectin, ivermectin, abamectin and/or moxidectin.

The solution may comprise a concentration of the metal(s) of at least 20 to 60 mg/ml.

Yet further according to the invention, a method of preparing a trace element solution comprising at least one metal selected from the group comprising selenium, copper, zinc, manganese and chromium, said method including the steps of:
(a) preparing a $MnCO_3$ mixture in a container at a temperature of at least 60 degrees Celsius;
(b) adding an EDTA solution to the container and subsequently adding at least one metal compound selected from the group comprising ZnO, $CuCO_3$, $Na_2CO_3$, $MnSO_4$ and $FeCl_3$;
(c) adding at least compound selected from the group comprising $Na_2SeO_3$ and $CrCl_3.6H_2O$ to the container to obtain the trace element solution;
(d) adjusting the pH of the trace element solution; and
(e) adding at least one component selected from the group comprising a vitamin, a vaccine, a growth stimulant, a dewormer, iron dextran, antibiotic and a synchronisation preparation.

The synchronisation preparation may be a combination of injectable hormonal preparations, inplantable hormonal preparations, intravaginal hormonal preparation and/or other slow release hormonal preparation.

The antibiotic(s) may include oral, injectable and/or implantable therapeutic remedies.

The antibiotic(s) may be used to treat and/or prevent infectious diseases.

The vaccine may include antigens and/or a combination of antigens and adjuvants.

The growth stimulants may include zeranol, estradiol, testosterone, progesterone and/or trenbolone acetate.

The dewormer may include macrocyclic lactones, leramizoles, benzimidazoles and/or salicylanilides.

The macrocyclic lactones may include doramectin, ivermectin, abamectin and/or moxidectin.

The solution may comprise a concentration of the metal(s) of at least 20 to 60 mg/ml.

Yet further according to the invention, a trace element solution comprises
(a) 20-50 mg/ml of zinc;
(b) 5-15 mg/ml manganese;
(c) 2.5-10 mg/ml selenium; and
(d) 10-20 mg/ml copper;
(e) at least one component selected from the group comprising a vitamin, a vaccine, a growth stimulant, a dewormer, iron dextran, an antibiotic and a synchronisation preparation.

The synchronisation preparation may be a combination of injectable hormonal preparations, inplantable hormonal preparations, intravaginal hormonal preparation and/or other slow release hormonal preparation.

The antibiotic(s) may include oral, injectable and/or implantable therapeutic remedies.

The antibiotic(s) may be used to treat and/or prevent infectious diseases.

The vaccine may include antigens and/or a combination of antigens and adjuvants.

The growth stimulants may include zeranol, estradiol, testosterone, progesterone and/or trenbolone acetate.

The dewormer may include macrocyclic lactones, leramizoles, benzimidazoles and/or salicylanilides.

The macrocyclic lactones may include doramectin, ivermectin, abamectin and/or moxidectin.

The solution may comprise a concentration of the metal(s) of at least 20 to 60 mg/ml.

The solution may comprise 5-10 mg/ml chromium.

The solution may comprise 5-120 mg/ml iron.

The solution may comprise 20-400 mg/ml iodine.

The vitamin, a vaccine, a growth stimulant, a dewormer, iron dextran, an antibiotic and a synchronisation preparation may be added and/or blended at any stage to the solution in the methods.

The vitamin, a vaccine, a growth stimulant, a dewormer, iron dextran, an antibiotic and a synchronisation preparation may be added and/or blended as an aqueous base.

DESCRIPTION OF EXAMPLES

The invention will now be described by way of example of injectable solutions in accordance with the invention.

Example 1

Example 1 relates to a method to prepare a trace element solution predominantly to be used for cattle and includes the mineral elements selenium, copper and chromium.

The method enables preparation of 25 liters of the solution containing 40 mg Zn, 10 mg Mn, 5 mg Se, 15 mg Cu and 5 mg Cr per ml.

A. Preparing $MnCO_3$

In a suitable container/drum, the $MnCO_3$ mud is prepared by adding solutions of 900 g $MnSO_4$ and 1150 g $Na_2CO_3$ together. The resultant mixture is decanted and washed three times.

B. Continuous Batch Process

To the $MnCO_3$ mud, hot water (70° C.) is added to a volume of at least 15 liters. Critical is the temperature at the start of the batch process which should be at least 60° C.

B.1 Preparing MnEDTA 2000 g EDTA and 500 g NaOH are weighed; the EDTA and NaOH are mixed; the EDTA/NaOH mixture is added to the drum, in small quantities to prevent excessive frothing, until the reaction is complete (leaving a clear pinkish solution).

B.2 Preparing ZnEDTA (2 steps)

Step 1:

2600 g EDTA, 690 g NaOH and 700 g ZnO are weighed, the EDTA and NaOH are mixed and ZnO is kept separate. The EDTA/NaOH mixture is added to the drum in small quantities to prevent boiling over, followed by addition of the ZnO. The reaction is allowed to complete (again leaving a clear pink solution). The temperature at this stage could reach 103° C.

Step 2:

2600 g EDTA, 690 g NaOH and 700 g ZnO are weighed. The EDTA and NaOH are mixed and the ZnO kept separate. The EDTA/NaOH mixture is added to the drum in small quantities to prevent boiling over, where after the ZnO is added. The reaction is allowed to complete (again leaving a clear pink solution). The temperature at this stage could reach 103° C.

B.3 Preparing CuEDTA 1760 g EDTA, 462 g NaOH and 693 g basic $CuCO_3$ are weighed. The EDTA and NaOH are mixed and the $CuCO_3$ kept separate. The EDTA/NaOH mixture is added to the drum, followed by careful addition of the $CuCO_3$, to prevent excessive frothing, and the reaction is allowed to complete (leaving a clear blue solution).

B.4 25 g chlorocresol is added and stirred till dissolved.

B.5 23 liters is made up

B.6 The mixture is allowed to cool to room temperature.

C. Final phase

C.1 303 g $Na_2SeO_3$ is added.

C.2 The pH is adjusted to 6.7 by adding NaOH (40% solution) or EDTA.

C.3 738 g EDTA, 192 g NaOH and 641 g $CrCl_3.6H_2O$ are weighed. The EDTA and NaOH are mixed and added to the drum. The $CrCl_3.6H_2O$ is added, whereby the reaction is slow.

C.4 The volume is made up to 25 liters.

Example 2

Example 2 relates to a method to prepare a trace element solution predominantly to be used for sheep and includes the mineral elements selenium and copper.

The method enables preparation of 100 liters of the solution containing 40 mg Zn, 10 mg Mn, 3 mg Se and 10 mg Cu per ml.

A. Preparing $MnCO_3$

In a suitable container/drum, the $MnCO_3$ mud is prepared by adding solutions of 3600 g $MnSO_4$ and 4600 g $Na_2CO_3$ together. The mixture is decanted and wash three times.

B. Continuous Batch Process

To the $MnCO_3$ mud, is added hot water (70° C.) to a volume of at least 60 liters. The temperature at the start of the batch process is critical and should be at least 60° C.

B.1 Preparing MnEDTA 8000 g EDTA and 2000 g NaOH are weighed. The EDTA and NaOH are mixed. The EDTA/NaOH mixture is added to the drum, in small quantities to prevent excessive frothing, until the reaction is complete (leaving a clear pinkish solution).

B.2 Preparing ZnEDTA (2 steps)

Step 1:

10400 g EDTA, 2760 g NaOH and 2800 g ZnO are weighed. The EDTA and NaOH are mixed and the ZnO kept separate. The EDTA/NaOH mixture is added to the drum in small quantities to prevent boiling over, followed by addition of the ZnO. The reaction is allowed to complete (again leaving a clear pink solution). The temperature at this stage could reach 103° C.

Step 2:

10400 g EDTA, 2760 g NaOH and 2800 g ZnO are weighed. The EDTA and NaOH are mixed and the ZnO kept separate. The EDTA/NaOH mixture is added to the drum in small quantities to prevent boiling over, followed by addition of the ZnO. The reaction is allowed to complete (again leaving a clear pink solution). The temperature at this stage could reach 103° C.

B.3 Preparing CuEDTA 4646 g EDTA, 1220 g NaOH and 1835 g basic $CuCO_3$ are weighed. The EDTA and NaOH are mixed and the $CuCO_3$ kept separate. The EDTA/NaOH mixture is added to the drum, followed by careful addition of the $CuCO_3$, to prevent excessive frothing, and the reaction is allowed to complete (leaving a clear blue solution).

B.4 100 g chlorocresol is added and the mixture stirred until dissolved.

B.5 The volume is made up to 96 liters

B.6 The mixture is cooled to room temperature.

C. Final phase

C.1 728 g $Na_2SeO_3$ is added.

C.2 The pH is adjusted to 6.7 by adding NaOH (40% solution) or EDTA.

C.3 The volume is made up to 100 liters.

Example 3

Example 3 relates to a method to prepare a trace element solution predominantly to be used for cattle and includes the mineral elements Selenium and Copper.

The method enables preparation of 100 liters of the solution containing 40 mg Zn, 10 mg Mn, 5 mg Se and 15 mg Cu per ml.

A. Preparing $MnCO_3$

In a suitable container/drum, the $MnCO_3$ mud is prepared by adding solutions of 3600 g $MnSO_4$ and 4600 g $Na_2CO_3$ together. The mixture is decanted and wash three times.

B. Continuous Batch Process

To the $MnCO_3$ mud, hot water (70° C.) is added to a volume of at least 60 liters. The temperature at the start of the batch process is critical and should be at least 60° C.

B.1 Preparing MnEDTA 7840 g EDTA and 1960 g NaOH are weighed. The EDTA and NaOH are weighed. The EDTA/NaOH mixture is added to the drum, in small quantities to prevent excessive frothing, until the reaction is complete (leaving a clear pinkish solution).

B.2 Preparing ZnEDTA (2 steps)

Step 1:

10400 g EDTA, 2760 g NaOH and 2800 g ZnO are weighed. The EDTA and NaOH are mixed and the ZnO kept separate. The EDTA/NaOH mixture is added to the drum, in small quantities to prevent boiling over, followed by addition of the ZnO. The reaction is allowed to complete (again leaving a clear pink solution). The temperature at this stage could reach 103° C.

Step 2:

10400 g EDTA, 2760 g NaOH and 2800 g ZnO are weighed. The EDTA and NaOH are mixed and the ZnO kept separate. The EDTA/NaOH mixture is added to the drum, in small quantities to prevent boiling over, followed by addition of the ZnO. The reaction is allowed to complete (again leaving a clear pink solution). The temperature at this stage could reach 103° C.

B.3 Preparing CuEDTA 7040 g EDTA, 1848 g NaOH and 2780 g basic $CuCO_3$ are weighed. The EDTA and NaOH is are mixed and the $CuCO_3$ kept separate. The EDTA/NaOH mixture is added to the drum, followed by careful addition of the $CuCO_3$, to prevent excessive frothing, and the reaction is allowed to complete (leaving a clear blue solution).

B.4 100 g chlorocresol is added and the mixture stirred until dissolved.

B.5 The mixture is made up to 96 liters

B.6 The mixture is allowed to cool to room temperature.

C. Final phase

C.1 1212 g $Na_2SeO_3$ is added.

C.2 The pH is adjusted to 7.0 by adding NaOH (40% solution) or EDTA.

C.3 The volume is made up to 100 liters.

General

In the examples, at least one component selected from the group comprising a vitamin, a vaccine, a growth stimulant, a dewormer, iron dextran, an antibiotic and a synchronisation preparation can be added and/or blended at any stage to the solution.

The synchronisation preparation include a combination of injectable hormonal preparations, inplantable hormonal preparations, intravaginal hormonal preparation and other slow release hormonal preparation. The antibiotics include oral, injectable and implantable therapeutic remedies. The antibiotic are used to treat and prevent infectious diseases.

The vaccine includes antigens or a combination of antigens and adjuvants. The growth stimulants include zeranol, estradiol, testosterone, progesterone and trenbolone acetate. The dewormer includes macrocyclic lactones, leramizoles, benzimidazoles and salicylanilides. The macrocyclic lactones includes doramectin, ivermectin, abamectin and moxidectin.

The vitamin, a vaccine, a growth stimulant, a dewormer, iron dextran, an antibiotic and a synchronisation preparation can be added and/or blended as an aqueous base.

The invention therefore provides a trace element solution which is tissue friendly, i.e. is not damaging or irritant to the tissue of animals and which comprises selenium, copper, zinc, manganese, iron and chromium and a component selected from the group comprising a vitamin, a vaccine, a growth stimulant, a dewormer, iron dextran, an antibiotic and a synchronisation preparation. The trace elements in solution are in a scientifically formulated ratio according to the post-absorption requirements of the animals calculated according to provided. As an example the trace element solution comprises
(a) 20-50 mg/ml of zinc;
(b) 5-15 mg/ml manganese;
(c) 2.5-10 mg/ml selenium;
(d) 10-20 mg/ml copper;
(e) 5-10 mg/ml chromium;
(f) 5-120 mg/ml iron;
(g) 20-400 mg/ml iodine; and
(h) at least one component selected from the group comprising a vitamin, a vaccine, a growth stimulant, a dewormer, iron dextran an antibiotic and a synchronisation preparation.

The iodine is provided in the form of potassium iodide or sodium iodide and the iron is provided in the form of iron chloride.

The method of preparing a trace element solution in accordance with the invention thus enables the production of a solution comprising an adequate trace mineral concentration and a component selected from the group comprising a vitamin, a vaccine, a growth stimulant, a dewormer, iron dextran, an antibiotic and a synchronisation preparation so that a 5 to 10 milliliter injection can make a significant impact on the trace mineral status of the animal, i.e. a practically applicable injectable supplement and a product that can improve the trace mineral status of an animal is provided. This is important as livestock producers will only inject livestock if a real benefit can be demonstrated. Furthermore, the subcutaneous injection is the preferred route to minimize tissue damage.

The invention claimed is:

1. An injectable trace element solution, produced from:
   (a) a first solution comprising selenium and metals zinc and manganese, wherein at least one of the metals is in the form of a complex with EDTA, the EDTA being selected from the group consisting of sodium EDTA, sodium hydroxide EDTA acid and potassium EDTA, and at least one addition metal selected from the group consisting of copper, chromium and iron, wherein the total concentration of selenium, zinc, manganese and said at least one additional metal is greater than 60 mg/ml;
   (b) a second solution comprising a dewormer and at least one other component selected from the group consisting of a vitamin, a vaccine, a growth stimulant, iron dextran, an antibiotic and a hormonal synchronization preparation; and
   (c) chlorocresol as a preservative;
   wherein injectable trace element solution is produced by combining the first solution and the second solution;
   wherein the first solution is produced in part by adding $Na_2SeO_3$ and $MnSO_4$;
   wherein the injectable trace element solution has a total concentration of selenium, zinc, manganese and said at least one additional metal of at least 60 mg/ml; and
   wherein the antibiotic has efficiency to treat or limit the occurrence of infection diseases.

2. The injectable trace element solution as claimed in claim 1, wherein the vaccine includes at least one compound selected from the group consisting of antigens and a combination of antigens and adjuvants.

3. The injectable trace element solution as claimed in claim 1, wherein the growth stimulants include at least one compound selected from the group consisting of zeranol, estradiol, testosterone, progesterone and trenbolone acetate.

4. The injectable trace element solution as claimed in claim 1, wherein the dewormer includes at least one compound selected from the group consisting of macrocyclic lactones, levamisole, benzimidazoles and salicylanilides.

5. The injectable trace element solution as claimed in claim 4, wherein the macrocyclic lactones include at least one compound selected from the group consisting of doramectin, ivermectin, abamectin and moxidectin.

6. The injectable trace element solution of claim 1, wherein its pH is between 6.7 and 7.0 inclusive.

7. A method for limiting the occurrence of a disease or disease condition or treating a disease condition selected from the group consisting of deficiency or suboptimal level of trace elements, infectious disease treatable by an antibiotic, parasitic worm infections, and vitamin deficiency, said method comprising administering to a patient in need of treatment therefrom, a therapeutically effective amount of an injectable trace element solution, the injectable trace element solution comprising:
   (a) a first solution comprising selenium and metals zinc and manganese, wherein at least one of the metals is in the form of a complex with EDTA, the EDTA being selected from the group consisting of sodium EDTA, sodium hydroxide EDTA acid and potassium EDTA, and at least one addition metal selected from the group consisting of copper, chromium and iron, wherein the total concentration of selenium, zinc, manganese and said at least one additional metal is greater than 60 mg/ml;
   (b) a second solution comprising a dewormer and at least one other component selected from the group consisting of a vitamin, a vaccine, a growth stimulant, iron dextran, an antibiotic and a hormonal synchronization preparation; and
   (c) chlorocresol as a preservative;
   wherein injectable trace element solution is produced by combining the first solution and the second solution;
   wherein the first solution is produced in part by adding $Na_2SeO_3$ and $MnSO_4$;
   wherein the injectable trace element solution has a total concentration of selenium, zinc, manganese and said at least one additional metal of at least 60 mg/ml; and
   wherein the antibiotic has efficiency to treat or limit the occurrence of infection diseases.

8. The method of claim 7, wherein the disease condition is an infectious disease.

\* \* \* \* \*